(12) United States Patent
Li et al.

(10) Patent No.: US 11,260,377 B2
(45) Date of Patent: Mar. 1, 2022

(54) METHOD FOR SYNTHESIZING A FER/MOR COMPOSITE MOLECULAR SIEVE

(71) Applicants: Dalian Institute of Chemical Physics, Chinese Academy of Sciences, Dalian (CN); BP (China) Holdings Limited, Shanghai (CN)

(72) Inventors: Xiujie Li, Dalian (CN); Shenglin Liu, Dalian (CN); Xiangxue Zhu, Dalian (CN); Sujuan Xie, Dalian (CN); Longya Xu, Dalian (CN); Zhiqiang Yang, Shanghai (CN); Xuebin Liu, Shanghai (CN)

(73) Assignee: BP (China) Holdings Limited, Shanghai (CN)

( * ) Notice: Subject to any disclaimer, the term of this patent is extended or adjusted under 35 U.S.C. 154(b) by 176 days.

(21) Appl. No.: 15/541,092

(22) PCT Filed: Dec. 28, 2015

(86) PCT No.: PCT/CN2015/099183
§ 371 (c)(1),
(2) Date: Aug. 13, 2018

(87) PCT Pub. No.: WO2016/107514
PCT Pub. Date: Jul. 7, 2016

(65) Prior Publication Data
US 2019/0262814 A1     Aug. 29, 2019

(30) Foreign Application Priority Data
Jan. 4, 2015    (CN) .......................... 201510002835.5

(51) Int. Cl.
| | | |
|---|---|---|
| *B01J 29/80* | (2006.01) | |
| *B01J 29/18* | (2006.01) | |
| *B01J 29/65* | (2006.01) | |
| *B01J 37/03* | (2006.01) | |
| *B01J 37/04* | (2006.01) | |
| *C07C 5/25* | (2006.01) | |
| *C07C 5/27* | (2006.01) | |
| *C01B 39/02* | (2006.01) | |
| *C01B 39/26* | (2006.01) | |
| *C01B 39/44* | (2006.01) | |
| *B01J 35/00* | (2006.01) | |
| *B01J 29/06* | (2006.01) | |

(52) U.S. Cl.
CPC ............. *B01J 29/80* (2013.01); *B01J 29/18* (2013.01); *B01J 29/65* (2013.01); *B01J 35/0006* (2013.01); *B01J 37/031* (2013.01); *B01J 37/04* (2013.01); *C01B 39/023* (2013.01); *C01B 39/26* (2013.01); *C01B 39/44* (2013.01); *C07C 5/2518* (2013.01); *C07C 5/2775* (2013.01); *B01J 2029/062* (2013.01); *B01J 2229/62* (2013.01); *C07C 2529/18* (2013.01); *C07C 2529/65* (2013.01); *C07C 2529/80* (2013.01)

(58) Field of Classification Search
CPC ... B01J 29/65; B01J 29/18; B01J 29/80; B01J 2229/62; B01J 2029/062; B01J 35/0006; B01J 37/04; B01J 37/031; C07C 2529/18; C07C 2529/65; C07C 2529/80; C01B 39/26; C01B 39/44; C01B 39/023
USPC ...... 502/60, 63, 64, 67, 69, 70, 78; 423/700, 423/709, 710
See application file for complete search history.

(56) References Cited

U.S. PATENT DOCUMENTS

| | | | |
|---|---|---|---|
| 3,933,974 A | 1/1976 | Winquist | |
| 4,016,245 A | 4/1977 | Plank et al. | |
| 4,088,739 A * | 5/1978 | Vaughan | ................. C01B 39/44 423/709 |
| 8,728,969 B2 * | 5/2014 | Nesterenko | ............... B01J 29/40 502/60 |
| 2005/0255991 A1 * | 11/2005 | Levin | ........................ C07C 1/20 502/214 |
| 2013/0157840 A1 * | 6/2013 | Lai | ........................... B01J 29/06 502/67 |

FOREIGN PATENT DOCUMENTS

| | | |
|---|---|---|
| CN | 1565970 A | 1/2005 |
| CN | 101091920 A | 12/2007 |
| CN | 101190791 | 6/2008 |
| CN | 101514013 A | 8/2009 |

(Continued)

OTHER PUBLICATIONS

Yongjun Hu et al., Machine translation of CN 101190791, 2008.*

(Continued)

*Primary Examiner* — Elizabeth D Wood
(74) *Attorney, Agent, or Firm* — McDonnel Boehnen Hulbert & Berghoff LLP (57) ABSTRACT

This application consists of a method for the synthesis of a type of FER/MOR composite molecular sieve. That method consisting of mixing FER seed crystals, MOR seed crystals, a silicon source, water and an acid or alkali, thus yielding a reaction mixture; by adjusting the proportions of the seed crystals added, the silicon-aluminium proportion, acidity/alkalinity and other reaction conditions, it is possible to obtain a dual phase composite molecular sieve within which the proportions of the crystal phases may be adjusted. In the synthesis process to which the method of this application relates, there is no need to add any organic template, thus reducing the cost of the reaction, in addition to reducing likely environmental pollution, thus having major potential applications.

25 Claims, 3 Drawing Sheets

(56) References Cited

FOREIGN PATENT DOCUMENTS

| | | |
|---|---|---|
| CN | 101618884 A | 1/2010 |
| CN | 102464337 A | 5/2012 |
| CN | 102950018 | 3/2013 |
| CN | 103058212 | 4/2013 |
| CN | 103058219 | 4/2013 |
| CN | 104338554 | 2/2015 |
| JP | H0899033 A | 4/1996 |
| WO | WO-2009/055216 | 4/2009 |

OTHER PUBLICATIONS

Li Xiujie et al., Machine translation of CN 102950018, 2013.*
Li Xiujie et al., Machine translation of CN 104338554, 2015.*
Machine Translation of CN 1565967 A, Jan. 19, 2005.*
Li et al., Tokyo Conference abstract, "Synthesis and catalytic application of FER/MOR composite zeolite", 2014.*
Jongkind et al. Synthesis and Characterization of Zeolites Using Saturated Cyclic Amines as Structure-Directing Agents, Microporous Materials, Elsevier Science BV, vol. 10, No.
Pinar et al., Synthesis of Ferrierite from Gels Containing a Mixture of Two Templates, Collection Symposium Series XIIIth Symposium on Chemistry of Nucleic Acid Components Spl.
Cheng, et al. FER Zeolite Crystallization in THF-Na "20-SiO"2-Al"2-"3-H"2-reactant System Containing Catalytic Amount of Organic Additives, Microporous and Mesoporous Materia.
Traa et al., Controlled Co-Crystallization of Zeolites A and X, Journal of Materials Chemicstry, vol. 12, No. 3, pp. 496-499, Feb. 6, 2002.
J. Pieterse et al., Structure-Activity Correlations for TON, FER, and MOR in the Hydroisomerization of n-Butain, Journal of Catalysis, vol. 195, No. 2, Oct. 25, 2000.

* cited by examiner

METHOD FOR SYNTHESIZING A FER/MOR COMPOSITE MOLECULAR SIEVE

FIELD OF INVENTION

This application belongs to the technical fields of materials chemistry and catalytic chemistry, in particular it relates to a method for the synthesis of a type of FER/MOR composite molecular sieve.

BACKGROUND TECHNOLOGY

FER molecular sieve is a type of laminar molecular sieve material that has a Ferrierite zeolite topographical structure (U.S. Pat. No. 4,016,245), which belongs to the orthorhombic crystals family and which possesses a perpendicularly intersecting two-dimensional channels system, having ten-membered channels being roughly 0.4×0.54 nm in size and eight-membered channels roughly 0.35×0.48 nm in size. Due to the suitability of the channels and its excellent thermal stability and acidity, it has been widely adopted in isomerization, polymerization, cracking and other such hydrocarbon conversion reaction processes. Traditional organic templates used in the synthesis of FER molecular sieves are mainly: ethylenediamine or pyrrolidine, butanediamine, 1,4-dimethyl-piperazine, hexamethyleneimine and cyclohexane.

MOR molecular sieve is a molecular sieve that has a Mordenite zeolite topographical structure, which has twelve-membered ring (around 0.67×0.70 nm) main channels which follow the C axis and parallel eight-membered ring (around 0.28×0.57 nm) side channels. Its excellent thermal stability and adjustable acidity has resulted in its wide adoption in the petrochemicals and fine chemicals fields.

The term composite molecular sieve refers to a co-crystallization product formed from two or more molecular sieves, being a composite crystal with the structural characteristics of two or more molecular sieves; this type of molecular sieve will generally exhibit characteristics that are different to those of single molecular sieves or the corresponding mechanically mixed materials. Due to composite molecular sieves having multiple structures and superimposed functions, the drawbacks of a single type of channel are overcome, making them advantageous in terms of molecular adsorption and diffusion and resulting in their having widespread potential applications in the refining catalysts field. Composite molecular sieves that have already been reported are MFI/MEL, BEA/MOR FAU/EMT, ST/SFF and OFF/ERI But in industrial manufacturing of traditional molecular sieves it is necessary to use an organic template. The use of an organic template not only increases production costs, but also results in environmental pollution.

Apart from this, the activity of composite molecular sieve catalysts is closely connected with the ratio of the two phases, whilst different catalytic reactions have different optimum ratios of the two phases.

Due to this, there is an urgent need to develop a green method allowing synthesis of composite molecular sieves of which the ratio of the crystal phase can be controlled and do not require the use of an organic template.

INVENTION SIMPLIFIED DESCRIPTION

This application consists of a type of FER/MOR composite molecular sieve, the synthesis of the FER/MOR composite molecular sieve being controlled by adjustment of the ratio of the seed crystal phases and the acidity/alkalinity of the synthesis system, yielding a dual-phase FER/MOR composite crystalline molecular sieve the ratio of the crystalline phases of which can be controlled, which doesn't require the addition of any organic template. The technical operations required by this method are simple, are environmentally friendly, are low in cost and result in a product with excellent crystalline properties, which has excellent potential in terms of its applications. This application also provides the FER/MOR composite molecular sieve synthesised using this method.

One aspect of this invention, is that this invention consists of a method for the synthesis of a type of FER/MOR composite molecular sieve, that method including the following steps: mixing of FER seed crystals, MOR seed crystals, a silicon source, water and an acid or alkali, thus yielding a reaction mixture; causing that reaction mixture to undergo a crystallization reaction, in order to obtain the FER/MOR composite molecular sieve, whereby the aforementioned crystallization reaction takes place under conditions whereby there is no organic template.

According to certain embodiments of this application, the aforementioned silicon source is solid silica gel, colloidal silica, sodium silicate, silicon dioxide, tetraethoxysilane, silicic acid or any mixture of these.

According to certain embodiments of this application, the aforementioned silicon source is $SiO_2$.

According to certain embodiments of this application, the aforementioned aluminium source is sodium metaaluminate, aluminium hydroxide, aluminium sulphate, boehmite or any mixture of these.

According to certain embodiments of this application, the aforementioned aluminium source is $Al_2O_3$.

According to certain embodiments of this application, the proportion of the total mass of FER seed crystals and MOR seed crystals accounted for by the FER seed crystals mass is 5-95%.

According to certain embodiments of this application, the proportion of the total mass of FER seed crystals and MOR seed crystals accounted for by the MOR seed crystals mass is 5-95%.

According to certain embodiments of this application, the proportion of the total mass of FER seed crystals and MOR seed crystals accounted for by the FER crystals mass is not less than 33%, 50%, 67%, 71% or 75%.

According to certain embodiments of this application, the aforementioned alkali is an inorganic alkali.

According to certain embodiments of this application, the aforementioned inorganic alkali is either sodium hydroxide, potassium hydroxide, ammonium hydroxide or any mixture of these.

According to certain embodiments of this application, the aforementioned acid is an inorganic acid.

According to certain embodiments of this application, the aforementioned inorganic acid is either sulphuric acid, hydrochloric acid, nitric acid or any mixture of these.

According to certain embodiments of this application, the pH of the reaction mixture is 9 or above.

According to certain embodiments of this application, the ratio between the $OH^-$ and the mol number of atomic aluminium within the reaction mixture is between 1.25:1 and 15:1.

According to certain embodiments of this application, the mass of FER seed crystals or MOR seed crystals is between 0.1-15.0% of total of the converted mass of atomic silicon or the converted mass of atomic aluminium within the aforementioned reaction mixture.

According to certain embodiments of this application, the ratio between the mol number of atomic silicon and the mol number of atomic aluminium within the reaction mixture is between 2.5:1 and 25:1.

According to certain embodiments of this application, the ratio between the water and the atomic aluminium mol number within the reaction mixture is between 100:1 and 1000:1.

According to certain embodiments of this application, the aforementioned crystallization reaction includes subjecting the reaction mixture to a reaction under conditions of self-generated pressure and a temperature of between 140-220° C. for between 20-120 hours.

According to certain embodiments of this application, the aforementioned crystallization reaction takes place in a reactor which includes a rotating oven, the rate of rotation of the rotating oven being between 30-100 rpm.

According to certain embodiments of this application, prior to commencing the crystallization reaction, pre-crystallization of the reaction mixture takes place under conditions of 80-120° C. for between 4-24 hours.

According to certain embodiments of this application, the aforementioned pre-crystallization takes place in a reactor with a rotating oven, the speed of rotation of that rotating oven being between 30-100 rpm.

According to certain embodiments of this application, after the aforementioned crystallization reaction has taken place, this also includes separation of the resultant FER/MOR composite molecular sieve.

According to certain embodiments of this application, the aforementioned FER seed crystals and MOR seed crystals are processed by calcination prior to the mixing step.

According to certain embodiments of this application, the aforementioned FER seed crystals or MOR seed crystals are ammonium type molecular sieve, nitrogen type molecular sieve or sodium type molecular sieve.

According to certain embodiments of this application, this application provides an FER/MOR composite molecular sieve synthesised according to the method outlined in this application.

According to certain embodiments of this application, the FER crystal phase mass percentage of FER/MOR composite molecular sieve is 8%.

According to certain embodiments of this application, the FER crystal phase mass percentage of the FER/MOR composite molecular sieve is at least 13%, or at least 20%, or at least 40%, or at least 45%, or at least 65%, or at least 75%, or at least 83%.

Accordingly, another aspect of this application is that it provides a use for the FER/MOR composite molecular sieve synthesised according to the method outlined in this application in the skeletal isomerization of butene.

APPENDED DIAGRAM SIMPLIFIED DESCRIPTION

INVENTION DETAILED DESCRIPTION

This application provides a method for the synthesis of a type of FER/MOR composite molecular sieve, as well as an FER/MOR composite molecular sieve synthesised according to that method.

The method for the synthesis of a type of FER/MOR composite molecular sieve provided by this application includes the following steps: mixing FER seed crystals, MOR seed crystals, a silicon source, water and an acid or alkali, thus yielding a reaction mixture; that reaction mixture is then subjected to a crystallization reaction, yielding the FER/MOR composite molecular sieve, whereby that crystallization reaction takes place under circumstances where there is no organic template.

In this application, the term "FER seed crystals" refers to a single-phase crystalline material consisting of naturally or artificially synthesised Ferrierite zeolite. The main elements within the FER seed crystals are silicon, aluminium, coordinated oxygen atoms and inorganic cations, its basic structural units being three dimensional crystalline material with a skeletal structure formed from silicon-oxygen tetrahedrons or aluminium-oxygen tetrahedrons. The FER seed crystals have a ten-membered ring and eight-membered ring channel system. The FER seed crystals can be natural Ferrierite; alternatively they can be artificially synthesised FER molecular sieve, such as ZSM-35 molecular sieve, Sr-D Brewsterite zeolite, Na type Ferrierite zeolite or Ca—Na type Ferrierite zeolite. In certain embodiments of this application, the FER seed crystals are ZSM-35 molecular sieve.

The term "MOR seed crystals" used in this application refers to a single phase crystalline material consisting of either natural or artificial Mordenite zeolite. The main elements within the MOR seed crystals are silicon, aluminium, coordinated oxygen atoms and inorganic cations, its basic structural units being three dimensional crystalline material with a skeletal structure formed from silicon-oxygen tetrahedrons or aluminium-oxygen tetrahedrons. The MOR seed crystals have a twelve-membered ring and eight-membered ring channel system. The MOR seed crystals may be natural Mordenite zeolite; alternatively they may be artificially synthesised Mordenite zeolite molecular sieve. In certain embodiments of this application, the MOR seed crystals are natural Mordenite zeolite.

The term "silicon source" used in this application refers to a material containing silicon, which may be either pure silicon or a compound or mixture formed of a composite of silicon and other materials. In certain embodiments of this application, the aforementioned silicon source provides the silicon-oxygen tetrahedral structural units within the FER/MOR composite molecular sieve. In certain embodiments of this invention, the aforementioned silicon source is an oxide of silicon. In certain embodiments of this application, the aforementioned silicon source is $SiO_2$. In certain applications of this application, the aforementioned silicon source is solid silica gel, colloidal silica, sodium silicate, silicon dioxide, tetraethoxysilane, silicic acid or any mixture of these.

The term "aluminium source" used in this application refers to a material that contains aluminium, which may be pure aluminium or a compound or mixture formed of a composite of aluminium and other materials. In certain embodiments of this application, the aforementioned aluminium source provides the aluminium-oxygen tetrahedral structural units within the FER/MOR composite molecular sieve. In certain embodiments of this application, the aforementioned aluminium source is an oxide of aluminium. In certain embodiments of this application, the aforementioned aluminium source is $Al_2O_3$. In certain embodiments of this application, the aforementioned aluminium source is sodium metaaluminate, aluminium hydroxide, aluminium sulphate, boehmite (SB powder) or any mixture of these.

The term "FER/MOR composite molecular sieve" used in this application refers to a composite crystal which possesses the structural characteristics of FER and MOR molecular sieves, whereby the structure of that composite crystal contains both FER ten-membered ring channels and eight-membered ring channels and MOR twelve-membered ring channels and eight-membered ring channels, whereby that type of molecular sieve is not a simple mixed material consisting of mechanically mixed FER single-phase crystalline molecular sieve and MOR single-phase crystalline molecular sieve. FER/MOR composite molecular sieve possesses multiple structures and superimposed functions, providing many advantages in terms of molecular adsorption and diffusion. The FER/MOR composite molecular sieve may be eutectic.

In traditional molecular sieve synthesis methods an organic template is used. The organic template refers to a compound that generally acts as a structural guide during molecular sieve synthesis. Traditional organic templates mainly include ethylenediamine, pyrrolidine, butanediamine, 1,4-dimethyl-piperazine, hexamethyleneimine and cyclohexane. The use of an organic template results in increased costs, whilst after the molecular sieve has been generated, the molecular sieve must be subjected to calcining to eliminate the organic template from within it; during the calcining process, it is possible that the organic template does not undergo complete pyrolysis with the result that there are blocked channels within the zeolite, which then affects its performance. In this application consisting of a method for the synthesis of a type of FER/MOR composite molecular sieve, there is no organic template used. As a result of this, the manufacturing costs associated with the method for synthesis of FER/MOR composite molecular sieve to which this application relates are reduced, whilst the catalytic performance of the FER/MOR composite molecular sieve is increased.

The inventors where this application is concerned also discovered that by adjusting the proportions of FER and MOR seed crystals added to the initial reaction, it is possible to obtain a series of FER/MOR composite molecular sieves with different relative FER content. By adjusting the ratio of FER and MOR seed crystals added in the initial reaction, it is possible to obtain a dual-phase FER/MOR composite molecular sieve with adjustable crystalline phase proportions. The inventors where this application is concerned discovered that when the ratio between the mass of FER seed crystal added to the initial reaction and total mass of total FER seed crystals and MOR seed crystals was increased, the mass percentage of the FER crystal phase within the composite molecular sieve also increased; as the ratio between the mass of FER seed crystal added to the initial reaction and total mass of total FER seed crystals and MOR seed crystals was reduced, the mass percentage of the FER crystal phase within the composite molecular sieve was also reduced. In certain embodiments of this application, the ratio of the mass of the FER seed crystals added in the initial reaction to the total mass of the aforementioned FER seed crystals and MOR seed crystals is respectively 5-95%, or 5-90%, or 5-80%, or 5-70%, or 5-60%, or 5-50%, or 5-40%, or 5-30%, or 5-20%, or 5-10%, or 10-95%, or 20-95%, or 30-95%, or 40-95%, or 50-95%, or 60-95%, or 70-95%, or 80-95%, or 90-95%. According to certain embodiments of this application, the ratio of the mass of the MOR seed crystals added in the initial reaction to the total mass of the aforementioned FER seed crystals and MOR seed crystals is respectively 5-95%, or 5-90%, or 5-80%, or 5-70%, or 5-60%, or 5-50%, or 5-40%, or 5-30%, or 5-20%, or 5-10%, or 10-95%, or 20-95%, or 30-95%, or 40-95%, or 50-95%, or 60-95%, or 70-95%, or 80-95%, or 90-95%.

In certain embodiments, the ratio of the mass of the FER seed crystals added in the initial reaction to the total mass of the aforementioned FER seed crystals and MOR seed crystals is respectively not less than 5%, or 10%, or 20%, or 30%, or 40%, or 50%, or 60%, or 70%, or 80%, or 90%. In certain embodiments, the ratio of the mass of the FER seed crystals added in the initial reaction to the total mass of the aforementioned FER seed crystals and MOR seed crystals is respectively not more than 95%, or 90%, or 80%, or 70%, or 60%, or 50%, or 40%, or 30% or 20% or 10%. In certain embodiments of this application the ratio of the mass of the FER seed crystals added in the initial reaction to the total mass of the aforementioned FER seed crystals and MOR seed crystals is respectively not less than 33%, 50%, 67%, 71% or 75%.

The inventors where this application is concerned discovered that by adjusting the acidity/alkalinity of the system, it was possible to obtain a dual-phase FER/MOR composite molecular sieve the ratio of the crystalline phases of which could be controlled.

According to certain embodiments of this application, the aforementioned alkali is an inorganic alkali. According to certain embodiments of this application, the aforementioned inorganic alkali is either sodium hydroxide, potassium hydroxide, ammonium hydroxide or any mixture of these.

According to certain embodiments of this application, the aforementioned acid is an inorganic acid. According to certain embodiments of this application, the aforementioned inorganic acid is either sulphuric acid, hydrochloric acid, nitric acid or any mixture of these.

According to certain embodiments of this application, the pH of the reaction mixture is 9 or above. According to certain embodiments of this application, the pH of the aforementioned reaction mixture is between 9-14, or 10-14, or 11-14, or 12-14, or 13-14, or 9-10, or 9-11, or 9-12, or 9-13.

The inventors where this application is concerned discovered that by adjusting the alkalinity of the system, as the ratio between the $OH^-$ and the mol number of atomic aluminium within the reaction mixture increased, the mass percentage of the MOR crystal phase within the composite molecular sieve also increased; as the ratio between the $OH^-$ and the mol number of atomic aluminium within the reaction mixture decreased, the mass percentage of the MOR crystal phase within the composite molecular sieve also decreased. According to certain embodiments of this application, the ratio between the $OH^-$ and the mol number of atomic aluminium within the reaction mixture is between 1.25:1 and 15:1, or 1.25:1 and 10:1, or 1.25:1 and 5.1, or 1.25:1 and 2.5:1, or 2.5:1 and 15:1, or 5:1 and 15:1, or 10:1 and 15:1. In certain embodiments, the ratio between the OH⁻ and the mol number of atomic aluminium within the reaction mixture is not less than 1.25:1, or 2.5:1. In certain embodiments, the ratio between the OH⁻ and the mol number of atomic aluminium within the reaction mixture is not more than 15:1, or 10:1, or 5:1, or 2.5:1. In certain embodiments of this application, the ratio between the OH⁻ and the mol number of atomic aluminium within the reaction mixture is 1.8, 2.8, 3.0, 3.1, 3.5 or 4.5. In this application, the mol number of OH⁻ refers to hydroxyl radicles (OH⁻) within the solution, the source of the OH⁻ being the alkali and the product of the reaction, for instance $NaAlO_2$ or $Na_2O$ undergoing a reaction generating OH⁻.

According to certain embodiments of this application, the mass of FER seed crystals or MOR seed crystals is 0.1-15.0%, or 0.1-10.0%, or 0.1-5%, or 0.5-15.0%, or 1.0-15.0%, or 5.0-15.0%, or 10.0-15.0% of the total of the converted mass of atomic silicon or the converted mass of atomic aluminium within the aforementioned reaction mixture. In certain embodiments, the mass of FER seed crystals or MOR seed crystals is at least 0.1%, or 0.5%, or 1.0%, or 2.0%, or 5.0% of the total of the converted mass of atomic silicon or the converted mass of atomic aluminium within the aforementioned reaction mixture. In certain embodiments, the mass of FER seed crystals or MOR seed crystals is at most 15%, or 10% or 5% of the total of the converted mass of atomic silicon or the converted mass of atomic aluminium within the aforementioned reaction mixture. In certain embodiments of this application, the mass of FER seed crystals is 1.0%, 2.0%, 2.5%, 3.0%, 5.0%, 8.0% or 10% of the total of the converted mass of atomic silicon within the aforementioned reaction mixture or the converted mass of atomic aluminium within the aforementioned reaction mixture. In certain embodiments of this application, the mass of MOR seed crystals is 0.7%, 1.0%, 2.0%, 4.0%, 5.0%, or 10% of the total of the converted mass of atomic silicon within the aforementioned reaction mixture or the converted mass of atomic aluminium within the aforementioned reaction mixture.

In this application, the mol number of atomic silicon within the reaction mixture refers to the mol number of silicon atoms within the reaction mixture. In this application, the mol number of atomic aluminium within the reaction mixture refers to the mol number of aluminium atoms within the reaction mixture.

The formula for calculating the atomic silicon mol number within the reaction mixture is as follows:

> atomic silicon mol number within the reaction mixture=mass of the material containing silicon/the molecular mass of the material containing silicon×the number of atoms of silicon within the chemical formula of the material containing silicon.

The formula for calculating the atomic aluminium mol number within the reaction mixture is as follows:

> atomic aluminium mol number within the reaction mixture=mass of the material containing aluminium/the molecular mass of the material containing aluminium×the number of atoms of aluminium within the chemical formula of the material containing aluminium.

In this application, converted mass of atomic silicon within the reaction mixture refers to the mol number of atomic silicon within the reaction mixture corresponding to the mol number of the converted mass of $SiO_2$. In this application, converted mass of atomic aluminium within the reaction mixture refers to the mol number of atomic aluminium within the reaction mixture corresponding to the mol number of the converted mass of $Al_2O_3$. The formula for calculating the converted mass of atomic silicon within the reaction mixture, being the mass of $SiO_2$ calculated based on the mol number of atomic silicon within the reaction mixture, is as follows:

> converted mass of atomic silicon within the reaction mixture=mol number of atomic silicon within the reaction mixture×the molecular weight of $SiO_2$.

For instance, if there was 1 mol of atomic silicon within the reaction mixture, this corresponds to 1 mol of $SiO_2$, as a result of this the mass of $SiO_2$ after conversion is 1×60=60 g, therefore the converted mass of 1 mol of atomic silicon would be 60 g.

The converted mass of atomic aluminium within the reaction mixture, being the mass of $Al_2O_3$ calculated based on the mol number of atomic silicon within the reaction mixture, is as follows:

> converted mass of atomic aluminium within the reaction mixture=½×mol number of atomic silicon×the molecular weight of $Al_2O_3$.

For instance, if there was 1 mol of atomic aluminium within the reaction mixture, corresponding to 0.5 mol $Al_2O_3$, the mass of $Al_2O_3$ calculated would be 0.5×102=51 g, therefore the converted mass of 1 mol of atomic aluminium is 51 g.

In certain embodiments, by adjusting the proportion of atomic silicon and atomic aluminium, it is possible to obtain a dual-phase FER/MOR composite molecular sieve. According to certain embodiments of this application, the ratios of atomic silicon mol number to atomic aluminium mol number within the aforementioned reaction mixture are 2.5:1-25:1, or 2.5:1-20:1, or 2.5:1-15:1, or 2.5:1-10:1, or 2.5:1-5:1, or 5:1-25:1, or 10:1-25:1, or 15:1-25:1, or 20:1-25.1. In certain embodiments, the ratio of the atomic silicon mol number to atomic aluminium mol number is not less than 2.5:1, or 5:1, or 10:1, or 15:1. In certain embodiments, the ratio of the atomic silicon mol number to atomic aluminium mol number is not more than 25:1, or 20:1 or 150:1. In certain embodiments of this application, the ratio of the atomic silicon mol number to atomic aluminium mol number is 9:1, 10:1, 11:1, 11.5:1, 16.5:1 or 19.5:1.

In certain embodiments, the ratio of water and atomic aluminium mol number within the aforementioned reaction mixture is 100:1-1000:1, or 1000:1-750:1, or 100:1-500:1, or 100:1-250:1, or 250:1-1000:1, or 500:1-1000:1, or 750:1-1000:1. In certain embodiments, the ratio of water and atomic aluminium mol number is not less than 100:1, or 250:1, or 500:1. In certain embodiments, the ratio of water and atomic aluminium mol number is not more than 1000:1, or 750:1 or 500:1. In certain embodiments of this application, the ratio of water and atomic aluminium mol number is 309:1, 331:1, 387:1, 646:1, 650:1, 780:1 or 963:1.

According to the method of this application, the aforementioned FER seed crystals, MOR seed crystals, silicon source, aluminium source, water and acid or alkali may be mixed in any order using any method, to obtain the aforementioned reaction mixture. In certain embodiments of this application, ultra-sound dispersion and/or mixing are used to bring about the even mixing of the reaction mixture.

In certain embodiments of this application, the reaction mixture obtained is sealed in a reactor vessel to carry out the crystallization reaction.

In certain embodiments of this application, the aforementioned crystallization reaction includes subjecting the reaction mixture to a reaction under conditions of self-generated pressure and a temperature of between 140-220° C. for between 20-120 hours. In certain embodiments, the temperature of the crystallization reaction is 140-200° C., or 140-180° C., or 140-160° C., or 160-220° C., or 180-220° C., or 200-220° C. In certain embodiments, the temperature of the crystallization reaction is not less than 140° C., or 160° C., or 180° C. In certain embodiments, the temperature of the crystallization reaction does not exceed 220° C., or 200° C., or 180° C.

In certain embodiments, the crystallization reaction time is 20-120 hours, or 20-100 hours, or 20-80 hours, or 20-60 hours, or 20-40 hours, or 40-120 hours, or 60-120 hours, or 80-120 hours, or 100-120 hours. In certain embodiments, the crystallization reaction time is not less than 20 hours, or 40 hours, or 60 hours. In certain embodiments, the crystallization reaction time is not more than 120 hours, or 100 hours, or 80 hours, or 60 hours.

Based on certain embodiments of this application, the aforementioned crystallization reaction takes place under hydrothermal conditions, within a sealed container, a liquid acting as the medium, preparation of the crystals occurring at a certain temperature and self-generated pressure. In certain embodiments, the hydrothermal temperature is 140-220° C., or 140-200° C., or 140-180° C., or 140-160° C., or 160-220° C., or 180-220° C., or 200-220° C. In certain embodiments, the hydrothermal temperature is not less than 140° C., or 160° C., or 180° C. In certain embodiments, the hydrothermal temperature is not greater than 220° C., or 200° C., or 180° C.

According to certain embodiments of this application, the aforementioned crystallization reaction takes placed within a reactor that includes a rotating oven, the rate of rotation of that rotating oven being 30-100 rpm. In certain embodiments, the rate of rotation of the reactor is not less than 30 rpm, or 40 rpm, or 50 rpm, or 60 rpm, or 70 rpm, or 80 rpm, or 90 rpm. In certain embodiments, the rate of rotation of the reactor is not greater than 100 rpm, or 90 rpm, or 80 rpm, or 70 rpm, or 60 rpm, or 50 rpm, or 40 rpm. In certain embodiments of this application, the reactor is a reaction vessel or synthesis vessel, or a reactor vessel or synthesis vessel with a rotating oven.

In certain embodiments of this application, before the crystallization reaction takes place, the reaction mixture is subjected to pre-crystallization for 5-24 hours at 80-120° C. Pre-crystallization generally refers to slow formation of crystals, a process that provides a nucleus for the crystals. In certain embodiments, the pre-crystallization temperature is 80-120° C., or 80-110° C., or 80-100° C., or 80-90° C., or 90-120° C., or 100-120° C., or 110-120° C. In certain embodiments, the pre-crystallization temperature is not less than 80° C., or 90° C., or 100° C. In certain embodiments, the pre-crystallization temperature is not greater than 120° C., or 110° C., or 100° C.

In certain embodiments, the pre-crystallization time is 4-24 hours, or 8-24 hours, or 10-24 hours, or 12-24 hours, or 14-24 hours, or 16-24 hours, or 18-24 hours, or 20-24 hours, or 22-24 hours, or 4-22 hours, or 4-20 hours, or 4-18 hours, or 4-16 hours, or 4-14 hours, or 4-12 hours, or 4-10 hours, or 4-8 hours. In certain embodiments the pre-crystallization time is no less than 4 hours, or 8 hours, or 10 hours, or 12 hours, or 14 hours, or 16 hours, or 18 hours, or 20 hours, or 22 hours. In certain embodiments, the pre-crystallization time is not greater than 24 hours, not greater than 22 hours, not greater than 20 hours, not greater than 18 hours, not greater than 16 hours, not greater than 14 hours, or 12 hours, or 10 hours, or 8 hours.

According to certain embodiments of this application, the aforementioned pre-crystallization takes place in a reactor which includes a rotating oven, the rate of rotation of the aforementioned oven being 30-100 rpm. In certain embodiments, the rate of rotation of the aforementioned oven is not less than 30 rpm, or 40 rpm, or 50 rpm, or 60 rpm, or 70 rpm, or 80 rpm, or 90 rpm. In certain embodiments, the rate of rotation of the aforementioned oven is not higher than 100 rpm, or 90 rpm, or 80 rpm, or 70 rpm, or 60 rpm, or 50 rpm, or 40 rpm.

In certain embodiments of this application, after the crystallization reaction has taken place, this includes a further step of separation of the FER/MOR composite molecular sieve obtained. In certain embodiments, after the reactor vessel is cooled with running water, solid-liquid separation is achieved by centrifuging, thus separating the solid material from the mother liquor within the resultant mixture, the pH of the resultant solid then reaching 8-9 after washing in water, after which it is dried yielding the composite molecular sieve sample.

In certain embodiments of this application, an organic template contained within the FER seed crystals or MOR seed crystals is eliminated by calcining before the mixing stage.

FER seed crystal or MOR seed crystal molecular sieve can be subjected to exchange using current ionic exchange technology, this resulting in the replacement of inorganic cations such as sodium ions within the FER seed crystals or MOR seed crystals with other cations, for instance ammonium ions, hydrogen ions, magnesium ions, zinc ions or gallium ions, resulting in an ammonium type, hydrogen type, magnesium type, zinc type or gallium type molecular sieve. In certain embodiments, The FER seed crystals or MOR seed crystals are ammonium type molecular sieve, hydrogen type molecular sieve or sodium type molecular sieve.

According to the method of this application, by adjusting the proportion of FER and MOR seed crystals, it is possible to obtain an FER/MOR composite molecular sieve the crystal phase proportions of which can be adjusted. In the FER/MOR composite molecular sieve synthesised according to the method of this application, the mass percentage of the FER/MOR composite molecular sieve accounted for by the FER crystal phase is 0-100%. According to certain embodiments of this application, during synthesis of the FER/MOR composite molecular sieve, the mass percentage of FER/MOR composite molecular sieve accounted for by the FER crystal phase is at least 8%. According to certain embodiments of this application, during synthesis of the FER/MOR composite molecular sieve, the mass percentage of FER/MOR composite molecular sieve accounted for by the FER crystal phase is at least 13%, or 20%, or 40%, or 45%, or 65%, or 75% or 83%.

Figure 1A:
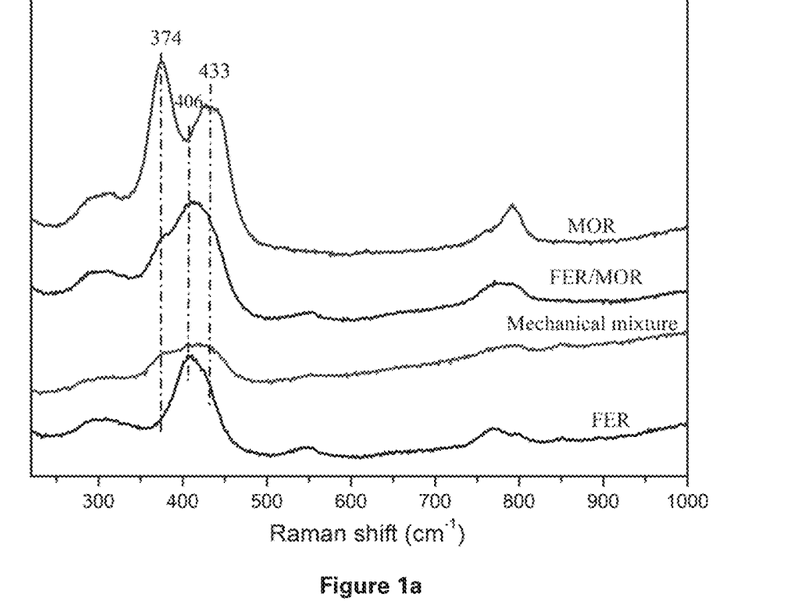
FIG. 1a is the UV-Raman spectrum of FER single-phase crystalline molecular sieve, MOR single-phase crystalline molecular sieve, FER/MOR composite molecular sieve, mechanically mixed FER single-phase crystalline molecular sieve and MOR single-phase crystalline molecular sieve.
Figure 1B:
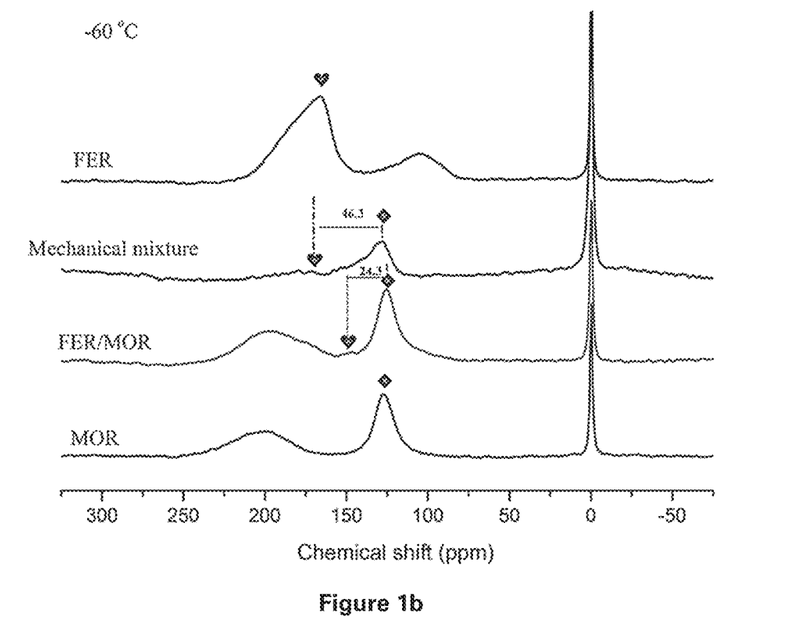
FIG. 1b is the hyperpolarized $^{129}Xe$ NMR spectrum of FER single-phase crystalline molecular sieve, MOR single-phase crystalline molecular sieve, FER/MOR composite molecular sieve, mechanically mixed FER single-phase crystalline molecular sieve and MOR single-phase crystalline molecular sieve.

By mechanically mixing single-phase FER crystalline molecular sieve with single-phase MOR crystalline molecular sieve it is possible to obtain a mechanical mixture. When compared with a mechanical mixture, the FER/MOR composite molecular sieve prepared according to this application is significantly different in terms of both structure and diffusion performance. As can be seen in the UV-Raman spectrum in FIG. 1a, it is possible to observe five-membered ring and four-membered ring vibration at the 374 $cm^{-1}$ peak and 433 $cm^{-1}$ peak of the MOR molecular sieve sample; the FER molecular sieve exhibits a five-membered ring vibration peak at around 406 $cm^{-1}$. In the UV-Raman spectrum corresponding to the mechanical mixture, the three peaks are superimposed, the peaks not having changed. Where the FER/MOR composite molecular sieve according to this application is concerned, the 406 and 433 cm$^{-1}$ peaks have coalesced, possibly indicating that the formation of a coexisting phase within the FER/MOR composite molecular sieve has led to changes in the T-O-T bond angle or the creation of new T-O-T bonds, whereby the T-O-T bonds referred to are the Si—O—Si bond or the Si—O—Al bond. In the low-temperature hyperpolarized $^{129}$Xe NMR spectrum (FIG. 1b) it can be seen that the exchange rate of Xenon (Xe) adsorbed within the 10-membered rings and 12-membered rings of the composite molecular sieve is significantly higher than that corresponding to the mechanical mixture, demonstrating that the composite molecular sieve possesses better channel interconnectivity. The above characterization results directly confirm that it is FER/MOR composite molecular sieve and not a simple mechanical mixture that has been prepared according to this application.

According to certain embodiments of this application, this application provides a sodium type FER/MOR molecular sieve, it being possible to modify that sodium type FER/MOR molecular sieve further using traditional ionic exchange technology allowing its use in different catalytic reactions. By supplementing this modified FER/MOR molecular sieve with a suitable substrate it is possible to use it in the manufacture of the catalysts required by various chemical reactions, thus allowing its use in catalytic reactions. In the skeletal isomerization of butene, the butene transformation rate, the isobutene specificity and the isobutene yield are all closely connected with the proportion of the two phases in the FER/MOR composite molecular sieve, whereby the optimal range of FER crystal phase mass proportion in terms of FER/MOR composite molecular sieve mass is 40-60%.

In this application, an X Pert Pro X-ray diffractometer manufactured by the Dutch company Panalytical was used, diffraction data in the 2θ=5-40° range being measured, yielding the mass percentage proportion of the FER crystal phase or MOR crystal phase within the FER/MOR composite molecular sieve. Here the CuK α radiation is that of a radiant tube, the tube voltage being 40 kV, the tube current being 50 mA, using CaF$_2$ (analytically pure) as the internal standard (reference may be made to: Zhang Ling et al. Small crystal ZSM-5/ZSM-11 composite molecular sieve synthesis. Petrochemical Technology. 2008, No. 37 Supplement: 556-558).

EXAMPLES

The following non-restrictive examples provide a more detailed description of this invention. It should be explained that, the presentation of the following examples is purely for the purpose of providing further description of the technical characteristics of this invention, and may not be interpreted as being for the purpose of restricting this invention. The following examples do not contain any detailed descriptions of traditional techniques (chemical synthesis technology etc.) the knowledge of which would be common to general technicians in this field.

Example 1: Preparation of FER/MOR Composite Molecular Sieve (1) Raw Materials:
Silicon source: 5.24 g of silicon dioxide (99.5 wt % SiO$_2$, 0.5 wt % H$_2$O);
Aluminium source: 2.64 g of sodium metaaluminate solution (NaAlO$_2$: 16.8 wt % Al$_2$O$_3$, 31.2 wt % NaOH, 52 wt % H$_2$O);
Alkali: 0.8 ml sodium hydroxide solution (0.1 g NaOH/ml);
Water: 45.5 g deionised water;
FER seed crystals: 0.283 g ZSM-35 molecular sieve;
MOR seed crystals: 0.113 g natural Mordenite zeolite.
SiO$_2$ mass=5.24×0.995=5.214 g; atomic silicon mol number=5.214/60=0.087 mol; atomic silicon converted mass (the mass of SiO$_2$ calculated from the atomic silicon mol number)=5.214 g; Al$_2$O$_3$ mass=2.64×0.168=0.444 g; atomic aluminium mol number=0.444/102×2=0.008 mol; atomic aluminium converted mass (the mass of Al$_2$O$_3$ calculated from the atomic aluminium mol number)=0.444 g; OH$^-$ mol number=(0.1×0.8+2.64×0.312)/40=0.0226 mol; H$_2$O mol number=(5.24×0.005+2.64×0.52+0.8−0.08+45.5)/18=2.65 mol.

The proportion of the total mass of FER seed crystals and MOR seed crystals accounted for by the FER seed crystals in the initial reaction=0.283/(0.283+0.113)×100%=71%. The pH of the reaction mixture was 11. The molar ratio of OH$^-$ to Al within the reaction mixture was OH$^-$/Al=0.0226/0.008=2.8:1, the molar ratio of Si to Al was Si/Al=0.087/0.008=11:1, the molar ratio of water to Al being H$_2$O/Al=2.65/0.008=331:1, The mass of FER seed crystals and MOR seed crystals being 5% and 2% of the summation of the atomic silicon converted mass and atomic aluminium converted mass (5.658 g) respectively.

(2) Procedural Steps

Figure 2:
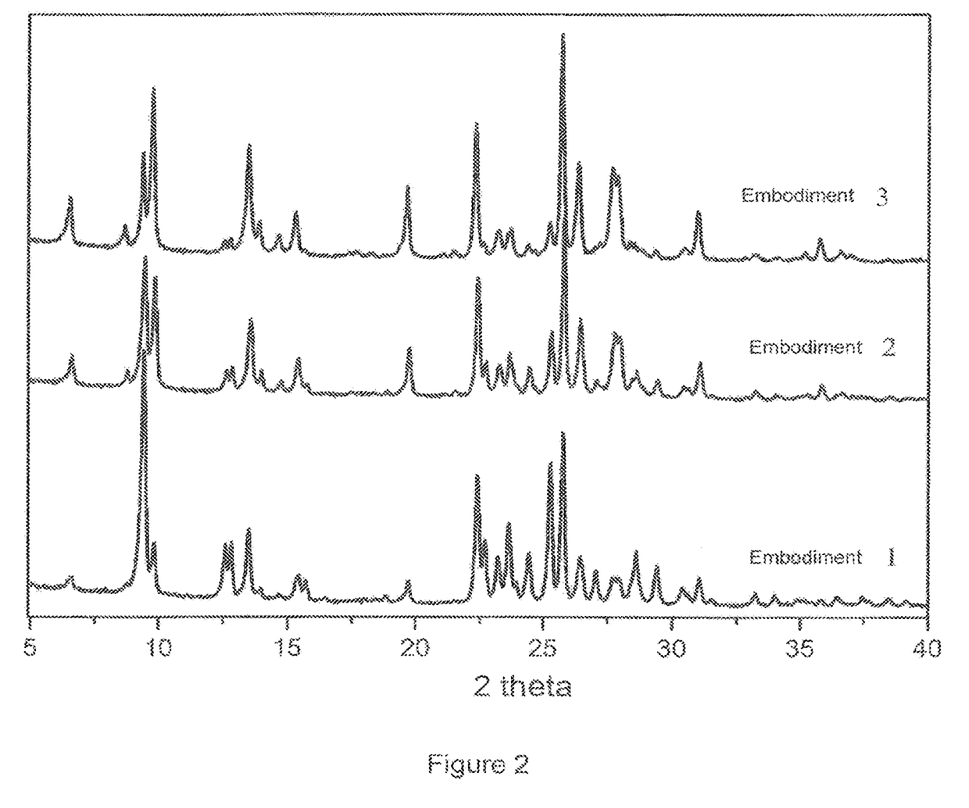
FIG. 2 is the X-ray diffraction (XRD) spectrum of the FER/MOR composite molecular sieve obtained according to examples 1, 2 and 3.
Figure 3:
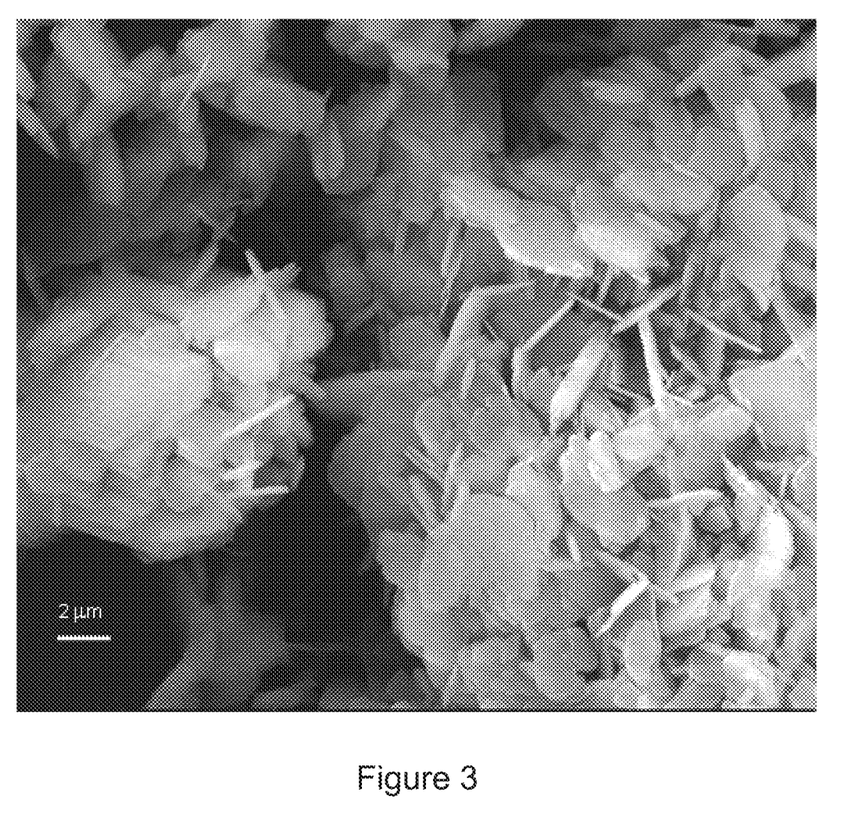
FIG. 3 is a scanning electron microscope (SEM) image of the FER/MOR composite molecular sieve obtained according to claim 1.

At the same time as mixing took place, 35.5 g of deionised water and the silicon source and sodium hydroxide solution were placed in that sequence within the reactor vessel, then mixing continued until they were evenly mixed; the FER seed crystals and MOR seed crystals were added to 10 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 100° C. for 10 hours, then the temperature was raised to 170° C. and it was left for a further 50 hours to undergo crystallization. During the pre-crystallization and crystallization processes, the rate of rotation of the rotating oven was 40 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected to X-ray diffraction (XRD) analysis, the result was as shown in FIG. 2, the product having the FER/MOR composite structure, the percentage mass ratio of FER crystal phase to FER/MOR composite molecular sieve being 75%, the percentage mass ratio of MOR crystal phase to FER/MOR composite molecular sieve being 25%; based on the SEM analysis, as can be seen in FIG. 3, the resultant FER/MOR composite molecular sieve exhibits the characteristics of having two coexisting phases.

Example 2: Preparation of FER/MOR Composite Molecular Sieve (1) Raw Materials:
Silicon source: 8.89 g of silicon dioxide (95 wt % SiO$_2$, 5 wt % H$_2$O);
Aluminium source: 3.91 g of sodium metaaluminate solution (NaAlO$_2$: 16.8 wt % Al$_2$O$_3$, 31.2 wt % NaOH, 52 wt % H$_2$O);

Alkali: 2.23 ml sodium hydroxide solution (0.1 g NaOH/ml);
Water: 135.0 g deionised water;
FER seed crystals: 0.1 g ZSM-35 molecular sieve;
MOR seed crystals: 0.1 g natural Mordenite zeolite.
$SiO_2$ mass=8.89×0.995=8.446 g; atomic silicon mol number=8.446/60=0.141 mol; atomic silicon converted mass (the mass of $SiO_2$ calculated from the atomic silicon mol number)=8.446 g; $Al_2O_3$ mass=3.91×0.168=0.657 g; atomic aluminium mol number=0.657/102×2=0.012 mol; atomic aluminium converted mass (the mass of $Al_2O_3$ calculated from the atomic aluminium mol number)=0.657 g; $OH^-$ mol number=(0.1×2.23+3.91×0.312)/40=0.0361 mol; $H_2O$ mol number=(8.89×0.05+3.91×0.52+2.23−0.223+135)/18=7.75 mol.

The proportion of the total mass of FER seed crystals and MOR seed crystals accounted for by the FER seed crystals in the initial reaction=0.1/(0.1+0.1)×100%=50%. The pH of the reaction mixture was 10. The molar ratio of OFF to Al within the reaction mixture was $OH^-/Al$=0.0361/0.012=3.0:1, the molar ratio of Si to Al was Si/Al=0.141/0.012=11.5:1, the molar ratio of water to Al being $H_2O$/Al=7.75/0.012=646:1, The mass of FER seed crystals and MOR seed crystals being 1% and 1% of the summation of the atomic silicon converted mass and atomic aluminium converted mass (9.103 g) respectively.

(2) Procedural Steps

At the same time as mixing took place, 105.0 g of deionised water and the silicon source and sodium hydroxide solution were placed in that sequence within the reactor vessel, then mixing continued until they were evenly mixed; FER seed crystals and MOR seed crystals were added to 30 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 120° C. for 5 hours, then the temperature was raised to 162° C. and it was left for a further 52 hours to undergo crystallization. During the pre-crystallization and crystallization processes, the rate of rotation of the rotating oven was 30 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected XRD analysis the resultant product was found to have the FER/MOR composite structure, the percentage mass ratio of FER crystal phase to FER/MOR composite molecular sieve being 40%, the percentage mass ratio of MOR crystal phase to FER/MOR composite molecular sieve being 60%.

Example 3: Preparation of FER/MOR Composite Molecular Sieve (1) Raw Materials:
Silicon source: 5.0 g of solid silica gel (92 wt % $SiO_2$, 8 wt % $H_2O$);
Aluminium source: 1.2 g of sodium metaaluminate solution ($NaAlO_2$: 16.8 wt % $Al_2O_3$, 31.2 wt % NaOH, 52 wt % $H_2O$);
Alkali: 3.4 ml sodium hydroxide solution (0.1 g NaOH/ml);
Water: 65.2 g deionised water;
FER seed crystals: 0.46 g ZSM-35 molecular sieve;
MOR seed crystals: 0.46 g natural Mordenite zeolite.

$SiO_2$ mass=5.0×0.92=4.6 g; atomic silicon mol number=4.6/60=0.077 mol; atomic silicon converted mass (the mass of $SiO_2$ calculated from the atomic silicon mol number)=4.6 g; $Al_2O_3$ mass=1.2×0.168=0.202 g; atomic aluminium mol number=0.202/102×2=0.004 mol; atomic aluminium converted mass (the mass of $Al_2O_3$ calculated from the atomic aluminium mol number)=0.202 g; $OH^-$ mol number=(0.1×3.4+1.2×0.312)/40=0.0179 mol; $H_2O$ mol number=(5.0×0.08+1.2×0.52+3.4−0.34+65.2)/18=3.85 mol.

The proportion of the total mass of FER seed crystals and MOR seed crystals accounted for by the FER seed crystals in the initial reaction=0.46/(0.46+0.46)×100%=50%. The pH of the reaction mixture was 10. The molar ratio of $OH^-$ to Al within the reaction mixture was $OH^-/Al$=0.0179/0.004=4.5:1, the molar ratio of Si to Al was Si/Al=0.077/0.004=19.5:1, the molar ratio of water to Al being $H_2O$/Al=3.85/0.004=963:1, The mass of FER seed crystals and MOR seed crystals being 10% and 10% of the summation of the atomic silicon converted mass and atomic aluminium converted mass (4.802 g) respectively.

(2) Procedural Steps

At the same time as mixing took place, 35.2 g of deionised water and the silicon source and sodium hydroxide solution were placed in that sequence within the reactor vessel, then mixing continued until they were evenly mixed; FER seed crystals and MOR seed crystals were added to 30 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 80° C. for 12 hours, then the temperature was raised to 170° C. and it was left for a further 36 hours to undergo crystallization. During the pre-crystallization and crystallization processes, the rate of rotation of the rotating oven was 60 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected to XRD analysis the resultant product was found to the FER/MOR composite structure, the percentage mass ratio of FER crystal phase to FER/MOR composite molecular sieve being 20%, the percentage mass ratio of MOR crystal phase to FER/MOR composite molecular sieve being 80%.

Example 4: Preparation of FER/MOR Composite Molecular Sieve (1) Raw Materials:
Silicon source: 52.28 g of colloidal silica (25.7 wt % $SiO_2$, 0.3 wt % $Na_2O$, 0.1 wt % $Al_2O_3$ and 73.9 wt % $H_2O$);
Aluminium source: 1.82 g of aluminium hydroxide (66.50 wt % $Al_2O_3$, 33.5 wt % $H_2O$);
Alkali: 15.72 ml sodium hydroxide solution (0.1 g NaOH/ml);
Water: 80.2 g deionised water;
FER seed crystals: 0.29 g ZSM-35 molecular sieve,
MOR seed crystals: 0.1 g natural Mordenite zeolite.

$SiO_2$ mass=52.28×0.257=13.436 g; atomic silicon mol number=13.436/60=0.224 mol; atomic silicon converted mass (the mass of $SiO_2$ calculated from the atomic silicon mol number)=13.436 g; $Al_2O_3$ mass=1.82×30.665+52.28×0.001=1.262 g; atomic aluminium mol number=1.262/102×2=0.024 mol; atomic aluminium converted mass (the mass of $Al_2O_3$ calculated from the atomic aluminium mol number)=1.262 g; OH⁻ mol number=(0.1×15.72)/40+(52.28× 0.003)×2/62=0.039+0.005=0.044 mol; $H_2O$ mol number= (52.28×0.739+1.82×0.335+15.72−1.572+80.2)/18=7.42 mol.

The proportion of the total mass of FER seed crystals and MOR seed crystals accounted for by the FER seed crystals in the initial reaction=0.29 (0.29+0.1)×100%=75%. The pH of the reaction mixture was 11. The molar ratio of OH⁻ to Al within the reaction mixture was OH⁻/Al=0.044/0.024=1.8:1, the molar ratio of Si to Al was Si/Al=0.224/0.024=9:1, the molar ratio of water to Al being $H_2O$/Al=7.42/0.024=309:1, The mass of FER seed crystals and MOR seed crystals being 2% and 0.7% of the summation of the atomic silicon converted mass and atomic aluminium converted mass (14.698 g) respectively.

(2) Procedural Steps t the same time as mixing took place, 50.2 g of deionised water and the silicon source and sodium hydroxide solution were placed in that sequence within the reactor vessel, then mixing continued until they were evenly mixed; FER seed crystals and MOR seed crystals were added to 30 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 120° C. for 10 hours, then the temperature was raised to 170° C. and it was left for a further 38 hours to undergo crystallization. During the pre-crystallization and crystallization processes, the rate of rotation of the rotating oven was 60 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected to XRD analysis the resultant product was found to have the FER/MOR composite structure, the percentage mass ratio of FER crystal phase to FER/MOR composite molecular sieve being 83%, the percentage mass ratio of MOR crystal phase to FER/MOR composite molecular sieve being 17%.

Example 5: Preparation of FER/MOR Composite Molecular Sieve (1) Raw Materials:
Silicon source: 7.31 g of solid silica gel (92 wt % $SiO_2$, 8 wt % $H_2O$);
Aluminium source: 0.67 g of SB powder (77.5 wt % $Al_2O_3$, 22.5 wt $H_2O$);
Alkali: 17.11 ml potassium hydroxide solution (0.1 g KOH/ml); 9.41 g of ammonium hydroxide (25.0 wt %, pH=10);
Water: 117.1 g deionised water;
FER seed crystals: 0.18 g ZSM-35 molecular sieve,
MOR seed crystals: 0.36 g natural Mordenite zeolite.
$SiO_2$ mass=7.31×0.92=6.72 g; atomic silicon mol number=6.725/60=0.112 mol; atomic silicon converted mass (the mass of $SiO_2$ calculated from the atomic silicon mol number)=6.725 g; $Al_2O_3$ mass=0.67×0.7751=0.519 g; atomic aluminium mol number=0.519/102×2=0.01 mol; atomic aluminium converted mass (the mass of $Al_2O_3$ calculated from the atomic aluminium mol number)=0.519 g; the OH⁻ mol number is the mol number of free OH⁻ within the solution. The OH⁻ mol number includes the mol number of free OH⁻ stemming from the potassium solution and the mol number of free OH⁻ stemming from the ammonium hydroxide. Based on the ammonium hydroxide having a pH of 10, the concentration of the ammonium hydroxide free H⁺ was $10^{-10}$ mol/L, the concentration of OH⁻ being $10^{-4}$ mol number=0.1×17.11/56+10⁻⁷× 9.41=0.0306 mol; $H_2O$ mol number=(7.31×0.08+0.67× 0.225+17.11−1.711+9.41×0.75+117.1)/18=7.8 mol.

The proportion of the total mass of FER seed crystals and MOR seed crystals accounted for by the FER seed crystals in the initial reaction=0.18/(0.18+0.36)×100%=33%. The pH of the reaction mixture was 10. The molar ratio of OH⁻ to Al within the reaction mixture was OH⁻/Al=0.0306/ 0.01=3.1:1, the molar ratio of Si to Al was Si/Al=0.112/ 0.01=11:1, the molar ratio of water to Al being $H_2O$/Al=7.8/ 0.01=780:1, the mass of FER seed crystals and MOR seed crystals being 2.5% and 5.0% of the summation of the atomic silicon converted mass and atomic aluminium converted mass (7.244 g) respectively.

(2) Procedural Steps

At the same time as mixing took place, 87.1 g of deionised water and the silicon source and potassium hydroxide solution were placed in that sequence within the reactor vessel, then mixing continued until they were evenly mixed; FER seed crystals and MOR seed crystals were added to 30 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 80° C. for 10 hours, then the temperature was raised to 180° C. and it was left for a further 48 hours to undergo crystallization. During the pre-crystallization and crystallization processes, the rate of rotation of the rotating oven was 90 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected to XRD analysis the resultant product was found to have the FER/MOR composite structure, the percentage mass ratio of FER crystal phase to FER/MOR composite molecular sieve being 13%, the percentage mass ratio of MOR crystal phase to FER/MOR composite molecular sieve being 87%.

Example 6: Preparation of FER/MOR Composite Molecular Sieve (1) Raw Naterials:
Silicon source: 21.4 g of tetraethoxysilane (28.0 wt % $SiO_2$, 72.0 wt % $H_2O$);
Aluminium source: 2.0 g of sodium metaaluminate solution ($NaAlO_2$: 16.8 wt %, $Al_2O_3$, 31.2 wt % $N_2OH$,
52 wt % $H_2O$);
Alkali: 2.2 ml sodium hydroxide solution (0.1 g NaOH/ml);
Water: 70.9 g deionised water;
FER seed crystals: 0.507 g ZSM-35 molecular sieve;
MOR seed crystals: 0.253 g natural Mordenite zeolite.
$SiO_2$ mass=21.4×0.28=5.992 g; atomic silicon mol number=5.992/60=0.100 mol; ×0.28=5.992 g; atomic silicon mol number=5.992/60=0.100 mol; atomic silicon converted mass (the mass of $SiO_2$ calculated from the atomic silicon mol number)=5.992 g; $Al_2O_3$ mass=2.0×0.168=0.336 g; atomic aluminium mol number=0.336/102×2=0.006 mol; atomic aluminium converted mass (the mass of $Al_2O_3$ calculated from the atomic aluminium mol number)=0.336 g; OH⁻ mol number=(0.1×2.2+2.0×0.312)/40=0.021 mol; $H_2O$ mol number=(21.4×0.72+2.0×0.52+2.2−0.22+70.9)/ 18=4.96 mol.

The proportion of the total mass of FER seed crystals and MOR seed crystals accounted for by the FER seed crystals in the initial reaction=0.507/(0.507+0.253)×100%=67%. The pH of the reaction mixture was 11. The molar ratio of OH⁻ to Al within the reaction mixture was OH⁻/Al=0.021/0.006=3.5:1, the molar ratio of Si to Al was Si/Al=0.100/0.006=16.5:1, the molar ratio of water to Al being $H_2O$/Al=4.96/0.006=827:1, the mass of FER seed crystals and MOR seed crystals being 8% and 4% of the summation of the atomic silicon converted mass and atomic aluminium converted mass (6.328 g) respectively.

(2) Procedural Steps

At the same time as mixing took place, 60.9 g of deionised water and the silicon source and sodium hydroxide solution were placed in that sequence within the reactor vessel, then mixing continued until they were evenly mixed; FER seed crystals and MOR seed crystals were added to 10 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 90° C. for 12 hours, then the temperature was raised to 165° C. and it was left for a further 64 hours to undergo crystallization. During the pre-crystallization and crystallization processes, the rate of rotation of the rotating oven was 60 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected to XRD analysis the resultant product had the FER/MOR composite structure, the percentage mass ratio of FER crystal phase to FER/MOR composite molecular sieve being 65%, the percentage mass ratio of MOR crystal phase to FER/MOR composite molecular sieve being 35%.

Example 7: Preparation of FER/MOR Composite Molecular Sieve (1) Raw Materials:
Silicon source: 4.8 g of silicon dioxide (99.5 wt % $SiO_2$);
Aluminium source: 2.4 g of sodium metaaluminate solution ($NaAlO_2$: 16.8 wt % $Al_2O_3$, 31.2 wt % NaOH, 52 wt % $H_2O$),
Alkali: 2.07 ml sodium hydroxide solution (0.1 g NaOH/ml);
Water: 52.7 g deionised water;
FER seed crystals: 0.1562 g ZSM-35 molecular sieve;
MOR seed crystals 0.0521 g natural Mordenite zeolite.
$SiO_2$ mass=4.8×0.995=4.776 g; atomic silicon mol number=4.776/60=0.0796 mol; atomic silicon converted mass (the mass of $SiO_2$ calculated from the atomic silicon mol number)=4.776 g; $Al_2O_3$ mass=2.4×0.168=0.403 g; atomic aluminium mol number=0.403/102×2=0.008 mol; atomic aluminium converted mass (the mass of $Al_2O_3$ calculated from the atomic aluminium mol number)=0.403 g; OH⁻ mol number=(0.1×2.07+2.4×0.312)/40=0.0239 mol; $H_2O$ mol number=(4.8×0.005+2.4×0.52+2.07−0.207+52.7)/18=3.10 mol.

The proportion of the total mass of FER seed crystals and MOR seed crystals accounted for by the FER seed crystals in the initial reaction=0.1562/(0.1562+0.0521)×100%=75%. The pH of the reaction mixture was 11. The molar ratio of OH⁻ to Al within the reaction mixture was OH⁻/Al=0.0239/0.008=3.0:1, the molar ratio of Si to Al was Si/Al=0.0796/0.008=10:1, the molar ratio of water to Al being $H_2O$/Al=3.10/0.008=387:1, The mass of FER seed crystals and MOR seed crystals being 3% and 1% of the summation of the atomic silicon converted mass and atomic aluminium converted mass (5.179 g) respectively.

(2) Procedural Steps

At the same time as mixing took place, 42.7 g of deionised water and the silicon source and sodium hydroxide solution were placed in that sequence within the reactor vessel, then mixing continued until they were evenly mixed; FER seed crystals and MOR seed crystals were added to 10 g of deionised water and ultrasound dispersion carried out after which they were added to the above mentioned mixture, then further mixing carried out until these were evenly mixed. The reaction mixture obtained was sealed in a reaction vessel with a rotating oven, then left to undergo pre-crystallization at 80° C. for 10 hours, then the temperature was raised to 160° C. and it was left for a further 64 hours to undergo crystallization. During the pre-crystallization and crystallization processes, the rate of rotation of the rotating oven was 40 rpm. The reactor vessel was then cooled with running water. The solid material and mother liquor were separated by centrifuging, then the solid material was washed with water until the pH was 8-9, then it was air dried at 100° C. for 8 hours, yielding the crystalline product. When subjected to XRD analysis, the resultant product was found to have the FER/MOR composite structure, the percentage mass ratio of FER crystal phase to FER/MOR composite molecular sieve being 45%, the percentage mass ratio of MOR crystal phase to FER/MOR composite molecular sieve being 55%.

When compared to example 4, the proportion of FER crystal phase to FER/MOR composite molecular sieve in example 7 was found to be the same as example 4, however in example 7 there was an increase in the mol ratio between OH⁻ and Al within the reaction mixture, which increased the proportion of the MOR crystal phase within the FER/MOR composite molecular sieve. As a result of this, when the proportion of the mass of FER seed crystals in terms of the total mass of FER seed crystals and MOR seed crystals remains constant, the mol ratio of OH⁻ to Al within the reaction mixture increases and the proportion of the MOR crystal phase within the FER/MOR composite molecular sieve increases; when the mol ratio of OH⁻ to Al within the reaction mixture drops, the proportion of the MOR crystal phase within the FER/MOR composite molecular sieve drops.

Example 8: Measurement of the Catalytic Performance of Catalyst within the 1-butene Skeletal Isomerization Reaction The FER/MOR composite molecular sieve products resulting from examples 1, 2 and 3 were placed in a 0.5 Mol/L ammonium nitrate solution and mixed for 2 hours, then ammonium ions were used to exchange the sodium ions within the molecular sieve, the solid material then being separated from the liquid by filtration, then the solid material was washed for 1 hour in deionised water, then the above mentioned exchange, filtration, washing, exchange and filtration steps were repeated, yielding the ammonium type molecular sieve. The ammonium type molecular sieve obtained was then calcined at 550° C. for 4 hours, then processed in an aqueous steam atmosphere at 550° C. for 3 hours, yielding the catalysts A, B and C.

Catalyst comparison: hydrogen type single-phase FER crystalline molecular sieve and single-phase MOR crystalline molecular sieve were mixed mechanically, yielding the catalyst D, within which the mass percentage ratio of FER molecular sieve was 40%, the mass percentage ratio of MOR molecular sieve being 60%.

Catalyst A, B, C and D reaction properties measurement testing:

Catalyst reaction property testing took place within a standard fixed bed reactor, the reactor tube having a diameter of 10 mm, a length of 32 cm and a catalyst load of 1 g. The catalyst was subjected to pre-processing at 500° C. in an $N_2$ atmosphere for 1 hour, then being cooled to room temperature within the $N_2$ atmosphere. Reaction conditions: temperature 400° C., pressure 0.1 MPa; 1-butene weight space velocity 8 $h^{-1}$; reaction raw material composition was: 1-butene 51.3%, $N_2$ 48.7% (volumetric proportion). The raw materials passed through the catalyst bed from the top downwards, reaction product being sampled at different reaction time points, online analysis of the composition of the resultant products being carried out using an $Al_2O_3$-plot chromatography column (manufactured by Agilent) and a Varian-3800 gas chromatograph (manufactured by the US company Varian) (reference: Shang Yongchen et al. The MCM-49 molecular sieve catalyst 1-butene skeletal isomerization reaction. Chinese Journal of Catalytics. 2004, 25 (2): 158-162). The method for calculating the yield Y of isobutene being as follows:

Y=quantity of isobutene produced/quantity of 1-butene material within the charge×100%.

The quantities of isobutene and 1-butene referred to are all molar quantities.

The isobutene yield in the 1-butene skeletal isomerization reaction using catalysts A, B, C and D is shown in table 1.

TABLE 1

Isobutene yield in the 1-butene skeletal isomerization reaction using catalysts A, B, C and D

| Catalyst | Isobutene yield % | | | | |
|---|---|---|---|---|---|
| (FER/MOR mass ratio) | 2 h | 10 h | 20 h | 40 h | 50 h |
| A (75:25) | 23 | 24 | 25 | 26 | 26 |
| B (40:60) | 21 | 26 | 28 | 32 | 36 |
| C (20:80) | 15 | 13 | 10 | 9 | 7 |
| D (40:60) | 14 | 20 | 22 | 25 | 30 |

From the reaction results shown in table 1, it can be deduced that isobutene yield from the 1-butene skeletal isomerization reaction is closely connected with the proportion of the two phases within the FER/MOR composite molecular sieve. Of the catalysts investigated, the sample from example 2, the FER mass percentage proportion of which was 40%, exhibited the best butene skeletal isomerization performance, with the highest resultant isobutene yield, whilst exhibiting excellent reaction stability. Although the FER crystal phase mass percentage proportion of the mechanically mixed single-phase FER crystalline molecular sieve and single-phase MOR crystalline molecular sieve was also 40%, the 1-butene skeletal isomerization performance of FER/MOR composite molecular sieve B was superior to that of the molecular sieve D consisting of mechanically mixed single-phase FER crystalline molecular sieve and single-phase MOR crystalline molecular sieve. In the 1-butene skeletal isomerization reaction, isobutene yield was closely connected with the proportion of the two phases within the FER/MOR composite molecular sieve, whilst the optimum range of the mass percentage proportion of the FER crystal phase within the FER/MOR composite molecular sieve was 40-60% (data not displayed).

EQUIVALENCE

It would be possible for a technician in this field to perceive or determine many equivalent technical schemes using research techniques that do not depart from those in general use based on the detailed embodiments and examples of this invention described by this text. As such this class of equivalent technical scheme shall be included in the scope covered by the appended claims.

All of the content of non-patent documents quoted throughout this document, the patent application and all of the content of the patent form an integral part of this text. Unless otherwise stated in the text, where the singular form "1", "a/an" and "the aforementioned" is used, this may also refer to a plural number. Furthermore, where this text uses the expression "containing" and/or "including" this refers to the appended characteristics, figures, steps, operations, components and/or parts, but does not exclude the existence or addition of one or more other characteristics, figures, steps, operations, components, parts and/or other combinations.

The sizes and values revealed in this text should not be considered as being restricted to the actual values recorded. In actual fact, unless otherwise stated, any such size recorded not only refers to the value recorded but also near values within a functionally equivalent range. For instance, where the size given is "40 mm" this may be taken to mean "about 40 mm".

Unless specifically excluded or restricted otherwise, any document quoted in this text, including any intersecting or related patent or patent application, shall be incorporated in this text in full due to having been quoted. The quotation of any document within this text does not represent recognizance of that document or its guidance or indications when taken in conjunction with any other reference documents or that the revelations of such inventions represent priority technology in terms of the invention revealed in this text or for which protection is requested. Furthermore, where the interpretation or definition of a term within this text contradicts the interpretation or definition of a similar term within a quoted document, the interpretation or definition of that term according to this text shall prevail.

Whilst this invention states and describes certain specific embodiments and examples, It would be possible for a technician in this field to be clearly aware of many alterations and modifications that could be made and where these do not depart from the principles and scope of this invention, such changes and modifications that conform to the principles and scope of this invention shall be included in the scope covered by the appended claims.

The invention claimed is:

1. A method for the synthesis of a type of FER/MOR composite molecular sieve, wherein that method includes the following steps:
   (a) mixing FER seed crystals, MOR seed crystals, a silicon source, an aluminium source, water and an acid or alkali to obtain a reaction mixture;
   (b) subjecting the reaction mixture to a crystallization reaction to obtain FER/MOR composite molecular sieve under conditions where there is no organic template present.

2. The method according to claim 1, wherein the silicon source is solid silica gel, colloidal silica, sodium silicate, silicon dioxide, tetraethoxysilane, silicic acid, or any mixture of these.

3. The method according to claim 2, wherein the silicon source is $SiO_2$.

4. The method according to claim 1, wherein the aluminium source is sodium metaaluminate, aluminium hydroxide, aluminium sulphate, boehmite, or any mixture of these.

5. The method according to claim 4, wherein the aluminium source is $Al_2O_3$.

6. The method according to claim 1, wherein the FER seed crystals are present at 5-95% by mass, based on the total mass of the FER seed crystals and the MOR seed crystals.

7. The method according to claim 1, wherein the MOR seed crystals are present at 5-95% by mass, based on the total mass of the FER seed crystals and the MOR seed crystals.

8. The method according to claim 1, wherein the FER crystals are present at not less than 33% by mass, based on the total mass of the FER seed crystals and the MOR seed crystals.

9. The method according to claim 1, wherein the alkali is used to obtain the reaction mixture, and the alkali is an inorganic alkali.

10. The method according to claim 9, wherein the inorganic alkali is sodium hydroxide, potassium hydroxide, ammonium hydroxide, or any mixture of these.

11. The method according to claim 1, wherein the acid is used to obtain the reaction mixture, and the acid is an inorganic acid.

12. The method according to claim 11, wherein the inorganic acid is sulphuric acid, hydrochloric acid, nitric acid, or any mixture of these.

13. The method according to claim 1, wherein the reaction mixture has a pH of 9 or above.

14. The method according to claim 1, wherein water and the aluminium source are present in the reaction mixture such that mole ratio between the alkali, measured as $OH^-$, and the aluminium source, measured as $Al^{3+}$ is between 1.25:1 and 15:1.

15. The method according to claim 1, wherein water, the silicon source and the aluminium source are present in the reaction mixture such that mole ratio between the silicon source, measures as $Si^{4+}$, and the aluminium source, measured as $Al^{3+}$, is between 2.5:1 and 25:1.

16. The method according to claim 1, wherein water and the aluminium source are present in the reaction mixture such that mole ratio between water and the aluminium source, measured as $Al^{3+}$, is between 100:1 and 1000:1.

17. The method of claim 1, wherein step (b) comprises subjecting the reaction mixture of step (a) to a reaction under conditions of self-generated pressure and a temperature of between 140-220° C. for between 20-120 hours.

18. The method of claim 1, wherein the crystallization reaction takes place in a reactor which includes a rotating oven, the rate of rotation of the rotating oven being between 30-100 rpm.

19. The method according to claim 1, further comprising a step of pre-crystallization of the reaction mixture takes place under conditions of 80-120° C. for between 4-24 hours between step (a) and step (b).

20. The method according to claim 19, wherein the pre-crystallization takes place in a reactor with a rotating oven, the speed of rotation of that rotating oven being between 30-100 rpm.

21. The method according to claim 1, further comprising the step of separating the FER/MOR composite molecular sieve after step (b).

22. The method of claim 1, wherein the FER seed crystals and MOR seed crystals are processed by calcination prior to the mixing step.

23. The method of claim 1, wherein the FER seed crystals or MOR seed crystals are ammonium type molecular sieve, nitrogen type molecular sieve or sodium type molecular sieve.

24. The method according to claim 1, wherein the FER seed crystals are present at 5-80% by mass, based on the total mass of the FER seed crystals and the MOR seed crystals.

25. The method according to claim 1, wherein the FER seed crystals are present at 30-80% by mass, based on the total mass of the FER seed crystals and the MOR seed crystals.

* * * * *